United States Patent
Harms

(10) Patent No.: US 9,687,609 B2
(45) Date of Patent: Jun. 27, 2017

(54) MOUNTING ARRANGEMENT AND COUPLING ASSEMBLY FOR A DRUG-DELIVERY DEVICE

(71) Applicant: SANOFI-AVENTIS DEUTSCHLAND GMBH, Frankfurt am Main (DE)

(72) Inventor: Michael Harms, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 15/214,915

(22) Filed: Jul. 20, 2016

(65) Prior Publication Data

US 2016/0325046 A1    Nov. 10, 2016

Related U.S. Application Data

(63) Continuation of application No. 15/172,331, filed on Jun. 3, 2016, which is a continuation of application (Continued)

(30) Foreign Application Priority Data

Mar. 31, 2009   (EP) ..................... 09004667

(51) Int. Cl.
*A61M 5/31* (2006.01)
*A61K 38/22* (2006.01)
(Continued)

(52) U.S. Cl.
CPC ............ *A61M 5/31* (2013.01); *A61K 9/0019* (2013.01); *A61K 38/2278* (2013.01);
(Continued)

(58) Field of Classification Search
CPC ........ A61M 5/3129; A61M 2005/3131; A61M 2005/3142; A61M 2005/3101;
(Continued)

(56) References Cited

U.S. PATENT DOCUMENTS

| 533,575 A | 2/1895 | Wilkens |
| 4,592,744 A * | 6/1986 | Jagger ............... A61M 5/002 600/576 |

(Continued)

FOREIGN PATENT DOCUMENTS

| EP | 0595507 | 5/1994 |
| EP | 0937476 | 8/1999 |

(Continued)

OTHER PUBLICATIONS

European Search Report for EP Patent Application No. 09004667, dated Oct. 20, 2009.
(Continued)

*Primary Examiner* — Emily Schmidt
*Assistant Examiner* — Lauren M Peng
(74) *Attorney, Agent, or Firm* — McDonnell Boehnen Hulbert & Berghoff LLP

(57) ABSTRACT

A mounting arrangement for a drug-delivery device is proposed, the mounting arrangement comprising: a plug element with a longitudinal axis (L) and a housing part having a recess with a side wall which is adapted to receive the plug element. At least one of the plug element or the side wall of the recess are provided with a protrusion for fixing the plug element in a given position relative to the housing part by a force-fit engagement. Furthermore, a coupling assembly is proposed, the coupling assembly comprising the plug element and the housing part being mechanically coupled to each other.

16 Claims, 3 Drawing Sheets

Related U.S. Application Data

No. 13/258,161, filed as application No. PCT/EP2010/054344 on Mar. 31, 2010, now Pat. No. 9,364,613.

(60) Provisional application No. 61/169,861, filed on Apr. 16, 2009.

(51) Int. Cl.

| | | |
|---|---|---|
| *A61K 38/26* | (2006.01) | |
| *A61M 5/315* | (2006.01) | |
| *A61K 9/00* | (2006.01) | |
| *A61K 38/28* | (2006.01) | |
| *A61M 5/24* | (2006.01) | |
| *A61M 39/26* | (2006.01) | |
| *A61M 39/22* | (2006.01) | |
| *F16K 3/24* | (2006.01) | |

(52) U.S. Cl.
CPC ............. *A61K 38/26* (2013.01); *A61K 38/28* (2013.01); *A61M 5/24* (2013.01); *A61M 5/31505* (2013.01); *A61M 39/22* (2013.01); *A61M 39/26* (2013.01); *A61M 2005/3142* (2013.01); *A61M 2039/266* (2013.01); *A61M 2202/07* (2013.01); *A61M 2202/30* (2013.01); *A61M 2207/00* (2013.01); *F16K 3/246* (2013.01); *Y10T 403/7026* (2015.01)

(58) Field of Classification Search
CPC ................ A61M 5/24; A61M 5/31505; A61M 2202/30; A61M 2202/07; A61M 2207/00; A61K 38/2278; A61K 38/26; A61K 9/0019; A61K 38/28
See application file for complete search history.

(56) References Cited

U.S. PATENT DOCUMENTS

| | | | |
|---|---|---|---|
| 4,634,092 A | | 1/1987 | Daniell et al. |
| RE33,219 E | | 5/1990 | Daniell et al. |
| 5,226,895 A | | 7/1993 | Harris |
| 5,279,586 A | | 1/1994 | Balkwill |
| 5,304,152 A | | 4/1994 | Sams |
| 5,320,609 A | | 6/1994 | Haber et al. |
| 5,334,162 A | * | 8/1994 | Harris ..................... A61J 1/062 604/232 |
| 5,383,865 A | | 1/1995 | Michel |
| 5,480,387 A | | 1/1996 | Gabriel et al. |
| 5,505,704 A | | 4/1996 | Pawelka et al. |
| 5,582,598 A | | 12/1996 | Chanoch |
| 5,626,566 A | | 5/1997 | Petersen et al. |
| 5,674,204 A | | 10/1997 | Chanoch |
| 5,688,251 A | | 11/1997 | Chanoch |
| 5,730,729 A | | 3/1998 | Bergstresser et al. |
| 5,921,966 A | | 7/1999 | Bendek et al. |
| 5,961,495 A | | 10/1999 | Walters et al. |
| 6,004,297 A | | 12/1999 | Steenfeldt-Jensen et al. |
| 6,193,698 B1 | | 2/2001 | Kirchhofer et al. |
| 6,221,046 B1 | | 4/2001 | Burroughs et al. |
| 6,235,004 B1 | | 5/2001 | Steenfeldt-Jensen et al. |
| 6,238,371 B1 | | 5/2001 | Himbert et al. |
| 6,248,095 B1 | | 6/2001 | Giambattista et al. |
| 6,541,802 B2 | | 4/2003 | Doyle |
| 6,899,698 B2 | | 5/2005 | Sams |
| 6,936,032 B1 | | 8/2005 | Bush, Jr. et al. |
| 7,241,278 B2 | | 7/2007 | Moller |
| 7,314,061 B2 | * | 1/2008 | Peppel .................. A61M 39/02 137/605 |
| 2002/0052578 A1 | | 5/2002 | Moller |
| 2002/0120235 A1 | | 8/2002 | Enggaard |
| 2003/0050609 A1 | | 3/2003 | Sams |
| 2003/0060807 A1 | * | 3/2003 | Tanghoj ............ A61M 25/0017 604/544 |
| 2004/0059299 A1 | | 3/2004 | Moller |
| 2004/0182393 A1 | | 9/2004 | MacMillan et al. |
| 2004/0210199 A1 | * | 10/2004 | Atterbury ......... A61M 5/31566 604/224 |
| 2004/0267207 A1 | | 12/2004 | Veasey et al. |
| 2005/0090427 A1 | * | 4/2005 | Moskowitz ........... A61K 9/006 424/49 |
| 2005/0113765 A1 | | 5/2005 | Veasey et al. |
| 2006/0153693 A1 | | 7/2006 | Fiechter et al. |
| 2007/0129671 A1 | * | 6/2007 | Mu ....................... A61M 5/315 604/82 |
| 2009/0182421 A1 | | 7/2009 | Silvestrini et al. |
| 2009/0275916 A1 | | 11/2009 | Harms et al. |

FOREIGN PATENT DOCUMENTS

| | | |
|---|---|---|
| EP | 0937471 | 9/1999 |
| EP | 1974761 | 10/2008 |
| WO | 99/38554 | 9/1999 |
| WO | 01/10484 | 2/2001 |
| WO | 03/076002 | 9/2003 |
| WO | 2007/118908 A1 | 10/2007 |
| WO | 2009/012406 | 1/2009 |

OTHER PUBLICATIONS

International Search Report for PCT Patent Application No. PCT/EP2010/054344, dated Jul. 19, 2010.

European Office Action for EP Application No. 10713440.5, dated Jan. 23, 2017.

\* cited by examiner

MOUNTING ARRANGEMENT AND COUPLING ASSEMBLY FOR A DRUG-DELIVERY DEVICE

CROSS REFERENCE TO RELATED APPLICATIONS

The present application is a continuation of U.S. patent application Ser. No. 15/172,331, filed Jun. 3, 2016, which is a continuation of U.S. patent application Ser. No. 13/258,161, filed Dec. 6, 2011, now U.S. Pat. No. 9,364,613, which is a U.S. National Phase Application pursuant to 35 U.S.C. §371 of International Application No. PCT/EP2010/054344 filed Mar. 31, 2011, which claims priority to European Patent Application No. 09004667.3 filed on Mar. 31, 2009 and U.S. Provisional Patent Application No. 61/169,861 filed Apr. 16, 2009. The entire disclosure contents of these applications are herewith incorporated by reference into the present application.

FIELD OF INVENTION

The present disclosure relates to a mounting arrangement and a coupling assembly with a housing part and a plug element suitable for use in a drug-delivery device. The drug-delivery device is preferably designed as a pen-type injector by which a number of predetermined or user-settable doses of a medical or pharmaceutical product can be administered. In particular, the present disclosure relates to a drug-delivery device which can be used by a person without formal medical training, e.g. advanced medical education.

BACKGROUND

Drug-delivery devices are in widespread use. For example, they can be applied by persons who do not have a formal medical background. Medical devices can be used to administer accurate and predefined doses of a medical product such as heparin or insulin. In particular, such devices can be used for a healthcare therapy whenever there is demand for a medical or pharmaceutical product being administered on a regular or an irregular basis over a short term or a long term period.

These circumstances set a number of requirements for the drug-delivery device of this kind which should be met. The device should be robust in construction, yet easy to use in terms of the manipulations of the parts, easily to be understood by the operator concerning the handling, and/or be suitable for an accurate delivery of the required dose of the medical or pharmaceutical product. Dose setting should be easy and unambiguous. In cases when the device is to be disposable rather than reusable, the device should be cheap to manufacture and easy to dispose of.

SUMMARY

The object of the invention is to provide a mounting device and a coupling assembly which are reliable and cheap to manufacture. The object is obtained by the features of the independent claims. Advantageous embodiments are disclosed in the sub claims.

According to a first aspect, a mounting arrangement for a drug-delivery device is provided. The mounting arrangement may comprise a plug element. The plug element may comprise a longitudinal axis. The mounting arrangement may comprise a housing part. The housing part may have a recess with a side wall which is adapted to receive the plug element. At least one of the plug element and the side wall of the recess may be provided with a protrusion. The protrusion may be adapted and arranged for releasably or permanently fixing the plug element in a given position relative to the housing part by a force-fit engagement.

This may enable a cheap manufacturing of the housing part and the plug element. Furthermore, by plugging the plug element into the recess of the housing part, a very reliable mechanical coupling may be established. In particular, the mechanical coupling may be suitable for use in a drug-delivery device requiring high precision with small tolerances for tiny mechanical components.

In a preferred embodiment, the longitudinal profile of the protrusion is inclined along a longitudinal end section of the protrusion for the purpose of facilitating the insertion of the plug element into the recess when establishing the force-fit engagement. This enables to reduce mechanical stress being exerted on the protrusion and the plug element and such may facilitate an accurate adjusting of the plug element relative to the housing part.

According to a further preferred embodiment, the longitudinal profile of the protrusion is inclined along the longitudinal end section such that the inclination is monotonous.

According to a further preferred embodiment, the inclination of the longitudinal profile is constant.

According to a further preferred embodiment, the longitudinal profile of the protrusion is arranged and designed such that the longitudinal angle between the longitudinal end section and the longitudinal axis is between 1° and 30°.

According to a further preferred embodiment, the longitudinal profile of the protrusion is designed such that it comprises the shape of a convex curve. This enables an easy plugging of the plug element into the recess of the housing part and increases a mechanical stability of the protrusion.

According to a further preferred embodiment, a longitudinal section of the protrusion is arranged adjacent to the longitudinal end section and has a constant radial distance relative to the longitudinal axis. This enables to increase a friction force of the force-fit engagement by increasing a contact surface between the protrusion and the plug element or the side wall of the recess and thus a reliable mechanical coupling.

According to a further preferred embodiment, a cross-section of the protrusion perpendicular to the longitudinal axis is designed such that the radial distance between the protrusion and the longitudinal axis decreases monotonously to a given minimum on a first side face. On a second side face which is adjacent to the first side face, the radial distance increases monotonously.

According to a further preferred embodiment, the cross-section is designed such that it has a triangular shape. This allows an easy manufacturing process of the protrusion. For example, the protrusion may be manufactured in a molding process.

According to a further preferred embodiment, the first side face and the second side face are arranged in an azimuth direction angle of about 60° relative to each other. This enables a high mechanical stability of the protrusion which still enables an easy and accurate mechanical coupling. A first edge between the first side face and the second side face may facilitate a guiding and fixing of the plug element into a predetermined position relative to the housing. In particular, the first edge may facilitate to guide and fix the plug element in a position such that the longitudinal axis of the plug element may be arranged congruently in regard to a longitudinal axis of the recess.

According to a second aspect, a coupling assembly for a drug-delivery device is provided. The coupling assembly may comprise a housing part having a recess with a side wall. The coupling assembly may further comprise a plug element with a longitudinal axis being arranged in the recess of the housing part at least partially. At least one of the plug element and the side wall of the recess may have a protrusion. The protrusion may be arranged at least partially in the recess of the housing part between the side wall of the recess and the plug element. The protrusion may be deformed in order to fix the plug element in a given position relative to the housing part in a force-fit engagement.

This may enable a very reliable mechanical coupling which may in particular be suitable for use in a drug-delivery device.

According to a further preferred embodiment, the coupling assembly comprises a plurality of protrusions. This enables a high mechanical stability by increasing friction forces with an increasing number of protrusions. This may further enable an accurate adjusting of the plug element relative to the housing part such that the plurality of protrusions facilitates a guidance of the plug element into a predetermined position relative to the housing part.

According to a further preferred embodiment, the plurality of protrusions is arranged such that any further axis running perpendicular to the longitudinal axis crosses at most one of the protrusions. This enables a reliable coupling assembly such that mechanical stress being exerted on the plug element and on the protrusions may be reduced. A precision of the adjustment may thus further be increased.

According to an embodiment, a drug-delivery device is provided. The device may comprise the previously described coupling assembly.

Preferably, at least two members of the drug-delivery device, e.g. a housing and a housing insert of the device, may be, releasably or permanently, coupled by means of the coupling assembly. The at least two members may be secured against translational and/or rotational movement with respect to each other by means of the coupling assembly.

According to an embodiment, the drug-delivery device is a pen-type device.

A pen-type device may comprise at least one, preferably two or more sleeves. These sleeves may be especially suited for being connected by means of the coupling assembly due to their essentially rotationally symmetrical shape.

According to a preferred embodiment, a mounting arrangement for a drug-delivery device comprises a plug element with a longitudinal axis and a housing part having a recess with a side wall which is adapted to receive the plug element, wherein at least one of the plug element and the side wall of the recess are provided with a protrusion for fixing the plug element in a given position relative to the housing part by a force-fit engagement.

According to a preferred embodiment, a coupling assembly for a drug-delivery device comprises
  a housing part having a recess with a side wall,
  a plug element with a longitudinal axis being arranged in the recess of the housing part at least partially,
  wherein at least one of the plug element and the side wall of the recess have a protrusion being arranged at least partially in the recess of the housing part between the side wall of the recess and the plug element and being deformed in order to fix the plug element in a given position relative to the housing part in a force-fit engagement.

BRIEF DESCRIPTION OF THE FIGURES

Further features and refinements become apparent from the following description of the exemplary embodiments in connection with the accompanying figures. The figures illustrate.

Elements of the same design or function are referenced by the same reference numerals in the figures.

DETAILED DESCRIPTION

Figure 1:
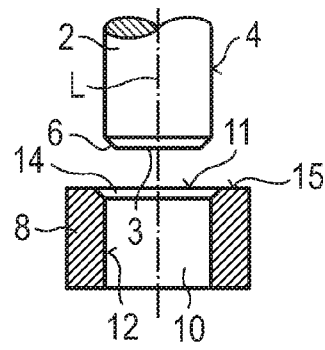
FIG. 1 is a mounting device comprising a plug element and a housing part with a recess.

FIG. 1 shows a mounting arrangement comprising a plug element 2 with a front surface 3 and a lateral surface 4. The plug element 2 further comprises a longitudinal axis L. A circumferential first chamfer 6 is arranged between the front surface 3 and the lateral surface 4. The mounting arrangement further comprises a housing part 8 having a recess 10 with an opening 11 and a side wall 12. A circumferential second chamfer 14 is arranged between the side wall 12 of the recess 10 and an upper side 15 of the housing part 8. In a preferred embodiment, the front surface 3 of the plug element 2 has the shape of a cylinder and the recess 10 of the housing part 8 has the shape of a hollow cylinder. The housing part 8 may be a sleeve, for example. Alternatively, the plug element 2 may be a sleeve (not explicitly shown), e.g. a hollow cylinder. Preferably, the diameter of the plug element 2 being shown in FIG. 1 is smaller than the diameter of the recess 10 in FIG. 1. The outer diameter of the plug element 2 is expediently smaller than the inner diameter of the recess 10 of the housing part 8.

Figure 2:
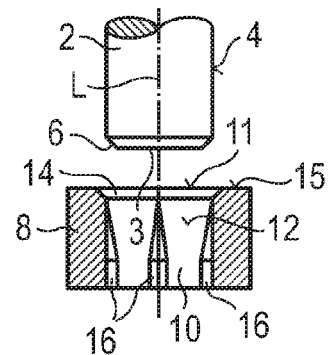
FIG. 2 is the mounting device with the housing part having protrusions, FIGS. 3A, B, C and D are a first embodiment of the protrusion, FIGS. 4A and B are a second embodiment of the protrusion.

FIG. 2 shows the mounting arrangement with the plug element 2 and the housing part 8. Three protrusions 16 are arranged on the side wall 12 of the recess 10. The protrusions 16 may also be arranged on the lateral surface 4 of the plug element 2. It is also possible that the protrusions 16 are arranged on the side wall 12 of the recess 10 as well as on the lateral surface 4 of the plug element 2. There may, for example, also be arranged five protrusions 16 on the side wall 12 of the recess. It is also possible that a different number of the protrusions 16 is arranged on the side wall 12 and/or the lateral surface 4. In the following, it will only be referred to the protrusion 16 in singular knowing that there may be a plurality of protrusions 16.

The mounting assembly is designed such that the plug element 2 and the housing part 8 can be mechanically coupled for establishing a coupling assembly. The coupling assembly can be such that the recess 10 receives the plug element 2 at least partially in order to fix it in a given position relative to the housing part 8. In particular, the plug element 2 can be arranged in the recess 10 such that its longitudinal axis L is in parallel to a longitudinal axis of the recess 10. The plug element 2 may for example be press fitted into the recess 10 of the housing part 8. The protrusions 16 may take up slack or play between plug element 2 and housing part 8, which may arise, for example, by the plug element 2 having an outer diameter which is less than the inner diameter of the recess of the housing part 8, if the protrusions 16 are disregarded. A minimal distance between two protrusions 16, which may face each other, is expediently less than the outer diameter of the plug element 2.

The housing part 8 and the plug element 2 are preferably parts for a drug deliver device. A sleeve for the plug element has the advantage that an element of the drive mechanism, such as the piston rod, may be moved through the housing part and the plug element during operation of the device.

The coupling assembly is designed to fix the plug element 2 in the given position relative to the housing part 8 by a force-fit engagement. The force-fit engagement is established between the protrusion 16 being arranged between the lateral surface 4 of the plug element 2 and the side wall 12 of the recess. In the case that the protrusion 16 is arranged on the lateral surface 4 of the plug element 2, the force-fit engagement is established between the protrusion 16 and the housing part 8 at the side wall 12 of the recess 8. In a preferred embodiment however, the protrusion 16 is arranged on the side wall 12 as shown in FIG. 2. In this case, the force-fit engagement is established between the protrusion and the plug element 2.

The plug element 2 and the recess 10 are designed such that with at least one protrusion 16 being arranged on the lateral surface 4 and/or the side wall 12, the protrusion 16 and/or the plug element 2 is deformed during the assembly when the plug element 2 is plugged into the recess 10. In a preferred embodiment, in the case that the protrusion 16 is arranged on the lateral surface 4 of the plug element 2, when the plug element 2 is plugged into the recess 10, the protrusion 16 and the plug element 2 are deformed and establish the force-fit engagement. In a further embodiment, the plug element 2 is made of a material having a smaller hardness in comparison to a hardness of the protrusion 16 such that the deformation rather concerns the plug element 2. The plug element 2 may be, for example, made of plastic. The mounting assembly is designed such that the housing part 8, except for the protrusion 16, is effectively prevented from being deformed. In particular, the housing part 8 can effectively be prevented from breaking.

If the protrusion 16 is arranged on the side wall 12 of the recess 10 as shown in FIG. 2, the force-fit engagement is established between the protrusions 16 and the plug element 2. However, it may also be possible that one or more protrusions 16 are arranged on the lateral surface 4 of the plug element 2. In this case, a force-fit engagement is established between the protrusion 16 and the side wall 12 of the housing part 8. There may, for example, protrusions 16 be arranged on the lateral surface 4 of the plug element 2 and on the side wall 12 of the housing part 8.

The protrusion 16 is arranged and designed such that its longitudinal profile in regard to the longitudinal axis L inclines along a longitudinal section 18. This may facilitate the insertion of the plug element 2 into the recess 10 during a manufacturing of the coupling assembly.

The protrusion 16 may, for example, be made in a molding process which is also known as die-casting. This may enable to manufacture the protrusion 16 integrally with the plug element 2 or the housing part 8, depending on where it shall be arranged. The protrusion 16 may also be made in a different process. In a preferred embodiment, a plurality of protrusions 16 is arranged on the side wall 12 of the recess 10 and/or on the lateral surface 4 of the plug element 2. In a further preferred embodiment, the plurality of protrusions 16 is arranged such that any further axis running perpendicular to the longitudinal axis L crosses at most one of the protrusions 16. This enables a reliable coupling such that a friction force can be increased in order to strengthen the force-fit engagement. The deformation of the protrusion 16 and/or the plug element 2 may be plastically and/or elastically.

Figure 3A:
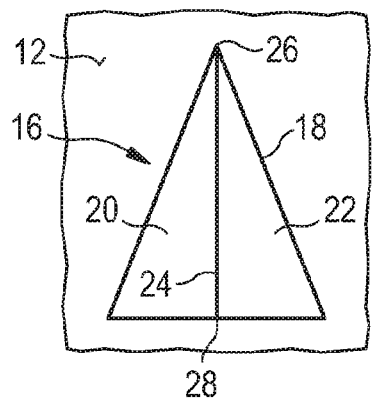

FIGS. 3A to 3D show a first embodiment of the protrusion 16. In the FIGS. 3A to 3D the protrusion 16 is arranged on the side wall 12 of the recess 10. However, the protrusion 16 may also be arranged on the lateral surface 4 of the plug element 2. FIG. 3A shows the first embodiment of the protrusion 16 in a front view. In the first embodiment, the protrusion 16 comprises a longitudinal end section 18 having a first side face 20 and a second side face 22, the first side face 20 and the second side face 22 being separated from each other by a first edge 24. In a longitudinal direction, the first edge 24 is arranged between a first corner 26 and a free corner 28. In the case when the protrusion 16 is arranged on the lateral surface 4 of the plug element 2, the first axial end 26 of the protrusion 16 is arranged in the direction towards the front surface 3 of the plug element 2. In the case when the protrusion 16 is arranged on the side wall 12 of the recess 10, the first axial end 26 of the protrusion is arranged in the direction towards the opening 11 of the recess 10.

Figure 3B:
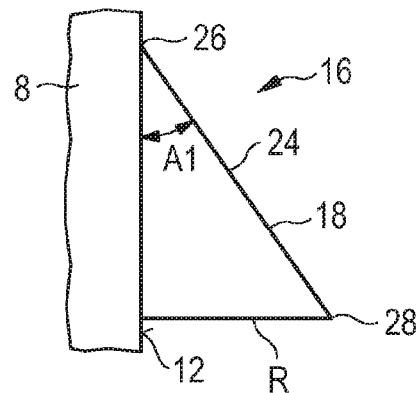

FIG. 3B shows the longitudinal profile of the protrusion 16 in regard to the longitudinal axis L. A radial distance R between the side wall 12 of the recess 10 and the free corner 28 can also be named as the radius of the protrusion 16. In a preferred embodiment, the protrusion 16 is designed such that the radial distance R increases with an increasing distance to the first axial end 26. The radial distance R of the protrusion may be, for example, 0.25 Millimeter. In other words, the longitudinal profile of the protrusion 16 inclines along the longitudinal end section 18. In a further preferred embodiment the longitudinal profile of the longitudinal end section 18 is designed such that the radial distance R increases at a constant rate with an increasing distance to the first axial end 26, as it is shown in the FIGS. 3B and 3D. In other words, the longitudinal profile of the longitudinal end section 18 is designed such that its inclination is constant. In a preferred embodiment, the longitudinal profile of the protrusion 16 is arranged and designed such that a longitudinal angle A1 between the longitudinal end section 18 and the longitudinal axis L is between 1° and 30°.

Figure 3C:
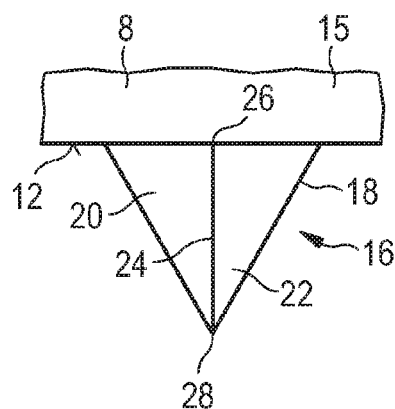

FIG. 3C shows the first embodiment of the protrusion 16 from an above view. The free edge 24 being arranged between the first axial end 26 and the free corner 28 can serve for guiding the plug element 2 relative to the housing part 8 during the mechanical assembly of the plug element 2 and the housing part 8. During the assembly, the first edge 24 may be cut into the plug element 16. As such, the first edge 24 may be designed as a cutting-edge.

Figure 3D:
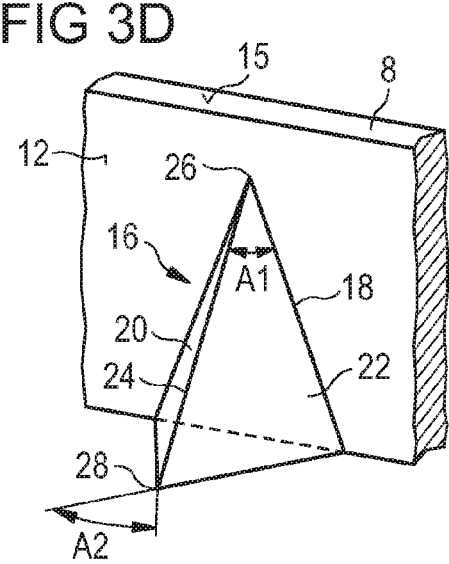

FIG. 3D shows the first embodiment of the protrusion 16 in a perspective view. An azimuth direction angle A2 between the first side face 20 and the second side face 22 may for example be between 15° and 90°. In a preferred embodiment, the azimuth direction angle A2 between the first side face 20 and the second side face 22 is about 60°. This enables a reliable coupling assembly such that on the one hand the azimuth direction angle A2 enables a high mechanical stability of the protrusion 16 preventing breakage and on the other hand, it is thin enough for enabling a deformation of the plug element 2 when being plugged into the recess 10.

Figure 4A:
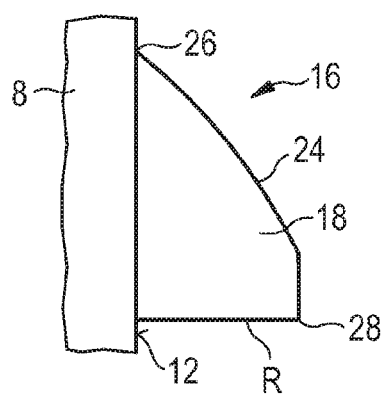
Figure 4B:
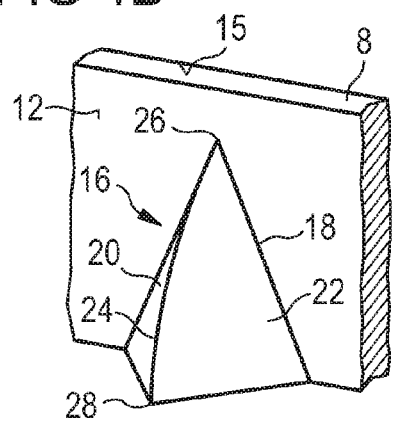

FIGS. 4A and 4B show a second embodiment of the protrusion 16. FIG. 4A shows the longitudinal profile of the protrusion 16. In a preferred embodiment, the free edge 24 between the first axial end 26 and the free corner 28 comprises a convex bending. The free edge 24 between the first axial end 26 and the free corner 28 may, for example, comprise a first part with a convex bending and second part being designed in parallel to the longitudinal axis L.

FIG. 4B shows the second embodiment of the protrusion 16 in a perspective view. In FIG. 4B the convex bending extends over the length of the free edge 24.

Figure 5:
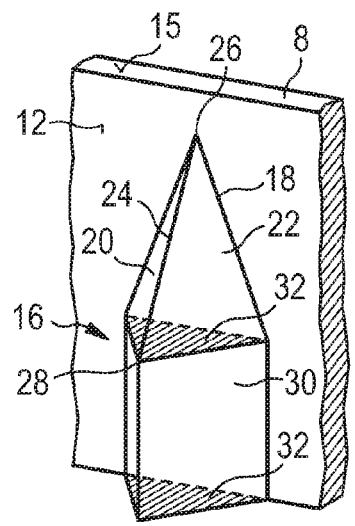
FIG. 5 is a third embodiment of the protrusion.
Figure 6:
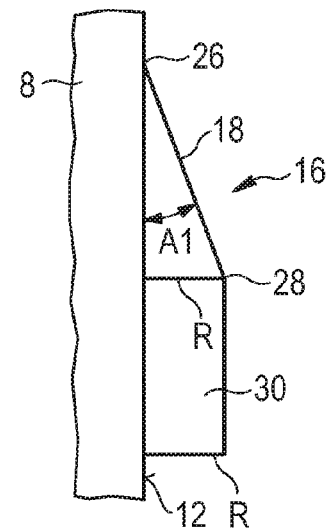
FIG. 6 is a longitudinal profile of the third embodiment.

FIGS. 5 and 6 show a third embodiment of the protrusion 16 from a perspective view and in the longitudinal profile respectively. The third embodiment of the protrusion 16 as shown in the FIGS. 5 and 6 comprises the longitudinal end section 18 as shown in FIGS. 3A to 3D and a longitudinal section 30 being arranged on an opposite side relative to the first axial end 26 of the longitudinal end section 18. However, the third embodiment of the protrusion 16 may also comprise the longitudinal end section 18 as shown in the FIG. 4A or 4B and the longitudinal section 18.

In a preferred embodiment, the radial distance R of the longitudinal section 30 is constant. This enables a reliable coupling assembly such that the friction of the force-fit engagement between the protrusion 16 and the housing part 8 or the lateral surface 4 of the plug element 2 respectively can be increased. The cross-section 32 of the longitudinal section 30 may be, for example, shaped as a triangle. The cross-section 32 of the longitudinal section 30 may also be shaped differently. In a preferred embodiment, the cross-section 32 of the protrusion 16 is designed such that in a direction perpendicular to the longitudinal axis L the radial distance R decreases monotonously to a given minimum and afterwards increases monotonously.

FIG. 6 shows the longitudinal profile of the third embodiment of the protrusion 16 comprising the longitudinal end section 18 and the longitudinal section 30.

Figure 7:
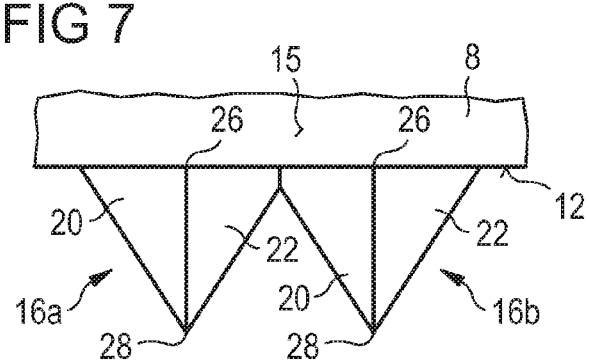
FIG. 7 is an arrangement of the protrusions.

FIG. 7 shows two protrusions 16 being arranged on the lateral surface such that the first side face 20 of a left-hand protrusion 16a is in contact with the second side face 22 of a right-hand protrusion 16b.

Figure 8:
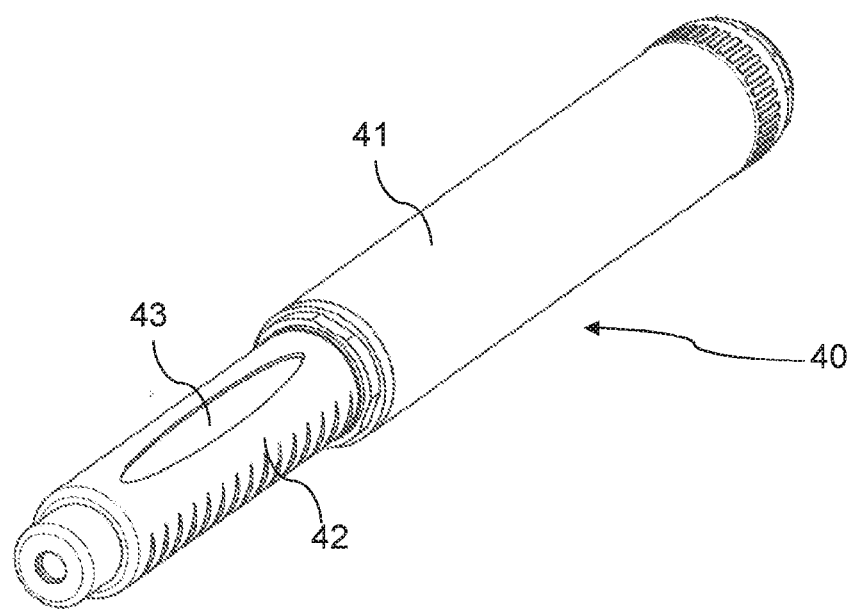
FIG. 8 is an exemplary embodiment of a drug-delivery device.

In FIG. 8 an exemplary embodiment of a drug-delivery device 40 is shown. The drug-delivery device 40 comprises a housing 41. The housing 41 comprises a tubular shape. The housing 41 may comprise or may be embodied as a sleeve. The housing 41 is configured to house members of the drug-delivery device 40, e.g. a guide member, a drive member and/or a dosing member (not explicitly shown). Preferably, these members may comprise or may be embodied as a sleeve, respectively. Accordingly, these members may be rotationally symmetric. The drug-delivery device 40 comprises a cartridge holder 42. The cartridge holder 42 is connectable, preferably releasably connectable, to the housing 41 of the device 40.

The drug-delivery device 40 may be an injection device. The device 40 may be a pen-type device, in particular a pen-type injector.

The device 40 comprises the previously described coupling assembly (not explicitly shown). The coupling assembly may be adapted and arranged for providing a reliable mechanical coupling between members of the device 40. Especially a pen-type device may comprise a plurality of sleeves. These sleeves may be especially suited for being coupled to each other by means of the coupling assembly due to their generally rotationally symmetric basic shape.

In particular, at least two members of the device 40, e.g. the housing 41 and the guide sleeve, may be permanently or releasably coupled by means of the coupling assembly. In particular, axial and/or rotational movement of these members of the device 40 may be prevented by means of the coupling assembly.

The device 40 comprises a cartridge 43. The cartridge 43 is retained in the cartridge holder 42. The cartridge holder 42 stabilizes the cartridge 43 mechanically. The cartridge 43 may hold a plurality of doses of a drug.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative; or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A pen-type drug injection device comprising:
a housing having a longitudinal axis and a recess with a side wall comprising at least two protrusions circumferentially spaced apart from each other and extending longitudinally, where each protrusion is deformable from a non-deformed shape to a deformed shape, where the non-deformed shape has longitudinal profile defined by a radial distance (R) measured relative to the side wall and perpendicular to the longitudinal axis; and
a plug,
wherein the plug is mechanically coupled within the recess by a force fit contact with a section of the longitudinal profile of the non-deformed shape to transform each protrusion to the deformed shape such that R is decreased in the section of the longitudinal profile that is in the force fit contact with the plug, where a friction force is caused by a deformation of the protrusion when the plug is coupled to the housing.

2. The device of claim 1 wherein the longitudinal profile of each protrusion has a constant radial distance (R).

3. The device of claim 1 wherein the housing is designed not to deform when the protrusion is deformed.

4. The device of claim 1 wherein the recess has an inner diameter greater than an outer diameter of the plug defining a play distance that is taken up by each protrusion.

5. The device of claim 1 wherein the plug is a sleeve.

6. The device of claim 5 wherein the sleeve is a cartridge configured to hold a drug.

7. The device of claim 6 wherein the drug comprises a pharmaceutical formulation containing at least one pharmaceutically active compound, wherein the pharmaceutically active compound has a molecular weight up to 1500 Da and/or is a peptide, a protein, a polysaccharide, a vaccine, a DNA, an RNA, an enzyme, an antibody, a hormone or an oligonucleotide.

8. The device of claim 6 wherein the drug comprises at least one peptide for the treatment and/or prophylaxis of diabetes mellitus or complications associated with diabetes.

9. The device of claim 6 wherein the drug comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

10. The device of claim 6, further comprising a cartridge holder configured to retain the cartridge.

11. The device of claim 5 wherein the sleeve is a cartridge holder configured to retain a cartridge configured to hold a drug.

12. The device of claim 1, wherein the plug comprises one or more deformable protrusion.

13. The device of claim 12, wherein the housing protrusions or the one or more plug deformable protrusion deforms plastically.

14. The device of claim 12, wherein the housing protrusions or the one or more plug deformable protrusion deforms elastically.

15. The device of claim 1, wherein a radial cross section of at least one of the protrusions changes along the longitudinal axis of the housing.

16. The device of claim 1, wherein the housing and the plug are rotationally symmetric.

* * * * *